(12) United States Patent
Starkebaum

(10) Patent No.: US 7,736,392 B2
(45) Date of Patent: Jun. 15, 2010

(54) BULKING OF UPPER ESOPHAGEAL SPHINCTER FOR TREATMENT OF OBESITY

(75) Inventor: Warren L. Starkebaum, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1172 days.

(21) Appl. No.: 11/117,060

(22) Filed: Apr. 28, 2005

(65) Prior Publication Data

US 2006/0247768 A1 Nov. 2, 2006

(51) Int. Cl.
*A61F 2/04* (2006.01)
(52) U.S. Cl. .................................. 623/23.64
(58) Field of Classification Search .............. 623/14.13, 623/23.72, 23.65, 23.64; 600/29, 30; 604/508; 606/157, 190, 191, 192; 128/898
See application file for complete search history.

(56) References Cited

U.S. PATENT DOCUMENTS

| 5,188,104 | A |  | 2/1993 | Wernicke et al. |
| 5,423,872 | A |  | 6/1995 | Cigaina |
| 5,782,798 | A |  | 7/1998 | Rise |
| 6,098,629 | A | * | 8/2000 | Johnson et al. ............. 128/897 |
| 6,231,613 | B1 |  | 5/2001 | Greff et al. |
| 6,251,063 | B1 |  | 6/2001 | Silverman et al. |
| 6,251,064 | B1 |  | 6/2001 | Silverman et al. |
| 6,277,392 | B1 |  | 8/2001 | Klein |
| 6,338,345 | B1 |  | 1/2002 | Johnson et al. |
| 6,358,197 | B1 |  | 3/2002 | Silverman et al. |
| 6,401,718 | B1 |  | 6/2002 | Johnson et al. |
| 6,427,089 | B1 |  | 7/2002 | Knowlton |
| 6,540,789 | B1 |  | 4/2003 | Silverman et al. |
| 6,592,859 | B1 |  | 7/2003 | Bley |
| 6,802,868 | B2 | * | 10/2004 | Silverman et al. ........ 623/23.65 |
| 7,037,344 | B2 | * | 5/2006 | Kagan et al. ............. 623/23.65 |
| 7,175,589 | B2 | * | 2/2007 | Deem et al. ................... 600/30 |
| 7,305,993 | B2 | * | 12/2007 | Tropsha et al. .............. 128/897 |
| 2002/0049363 | A1 |  | 4/2002 | Milbocker |
| 2002/0183768 | A1 |  | 12/2002 | Deem et al. |
| 2003/0008843 | A1 |  | 1/2003 | Shaw et al. |
| 2003/0040804 | A1 |  | 2/2003 | Stack et al. |
| 2003/0066536 | A1 | * | 4/2003 | Forsell ....................... 128/899 |
| 2003/0109931 | A1 |  | 6/2003 | Geitz |

(Continued)

FOREIGN PATENT DOCUMENTS

WO    WO 00/69376    11/2000

(Continued)

OTHER PUBLICATIONS

Starkebaum and Gerber, US Publication US 2005/0245957, filed Apr. 30, 2004, paragraph 0040.*

*Primary Examiner*—Thomas J Sweet
*Assistant Examiner*—Michael J Booth
(74) *Attorney, Agent, or Firm*—Shumaker & Sieffert, P.A.

(57) ABSTRACT

A method for treatment of obesity involves implantation of bulking devices within the upper esophageal sphincter (UES) to inhibit swallowing, thereby limiting food intake and treating obesity. One or more bulking devices are implanted within or near the UES to create a partial obstruction, partially impair UES muscle function, or both. The bulking devices make swallowing difficult, limiting the rate of food intake by a patient, and discouraging the patient from quickly consuming an excessive amount of food at one time.

35 Claims, 8 Drawing Sheets

U.S. PATENT DOCUMENTS

| | | |
|---|---|---|
| 2003/0109935 A1 | 6/2003 | Geitz |
| 2003/0158601 A1 | 8/2003 | Silverman et al. |
| 2003/0161887 A1* | 8/2003 | Klein .................. 424/489 |
| 2003/0188755 A1* | 10/2003 | Milbocker .............. 128/898 |
| 2004/0009224 A1 | 1/2004 | Miller |
| 2004/0019388 A1 | 1/2004 | Starkebaum |
| 2004/0030217 A1 | 2/2004 | Yeung et al. |
| 2004/0037865 A1 | 2/2004 | Miller |
| 2004/0248188 A1* | 12/2004 | Sanders .................. 435/7.1 |
| 2005/0096497 A1 | 5/2005 | Gerber et al. |
| 2005/0096751 A1 | 5/2005 | Gerber et al. |
| 2005/0245957 A1 | 11/2005 | Starkebaum |
| 2005/0246037 A1 | 11/2005 | Starkebaum |
| 2005/0247320 A1* | 11/2005 | Stack et al. .............. 128/898 |

FOREIGN PATENT DOCUMENTS

| | | |
|---|---|---|
| WO | WO 01/87335 | 11/2001 |

\* cited by examiner

BULKING OF UPPER ESOPHAGEAL SPHINCTER FOR TREATMENT OF OBESITY

FIELD OF THE INVENTION

The invention relates to medical devices and methods for treatment of obesity.

BACKGROUND

Obesity is a major health concern in the United States and other countries. A significant portion of the population is overweight with the number increasing every year. Obesity is one of the leading causes of preventable death. Obesity is associated with several co-morbidities that affect almost every body system. Some of these co-morbidities include: hypertension, heart disease, stroke, high cholesterol, diabetes, coronary disease, breathing disorders, sleep apnea, cancer, gallstones, and musculoskeletal problems.

Multiple factors contribute to obesity, including physical inactivity and overeating. A variety of medical approaches have been devised for treatment of obesity. Existing therapies include diet, exercise, appetite suppressive drugs, metabolism enhancing drugs, surgical restriction of the gastric tract, and surgical modification of the gastric tract. In general, surgery is reserved for patients in whom conservative measures, such as monitoring caloric intake or controlling appetite with appetite suppressants, have failed. In addition, surgery is generally reserved for patients who are seriously, and sometimes morbidly, overweight.

There are many surgical approaches to obesity. For example, one technique involves implantation of one or more bulking prostheses to reduce stomach volume. A bulking prosthesis and limits the amount of food the stomach can hold, causing a sensation of satiety. Another approach is restrictive surgery, which surgically makes the stomach smaller by removing or closing a section of the stomach. This procedure also reduces the amount of food the stomach can hold. Another surgical procedure is the gastric bypass procedure, in which a surgeon creates a small stomach pouch to restrict food intake and constructs a bypass of the duodenum and other segments of the small intestine. This procedure limits the amount of food that is completely digested or absorbed by the patient.

SUMMARY

In general, the invention is directed to medical devices and methods for treatment of obesity. The invention provides methods and devices for bulking the upper esophageal sphincter (UES) to inhibit swallowing, thereby limiting food intake and treating obesity. One or more bulking devices are implanted within or near the UES to create a partial obstruction or partially impair UES muscle function. In either case, the bulking devices make swallowing difficult, limiting the rate of food intake by a patient, and discouraging the patient from quickly consuming an excessive amount of food at one time.

With the bulking devices implanted within the UES, the patient is generally able to swallow, but with greater difficulty. When an excessive amount of food is consumed in a short period of time, the difficulty experienced during swallowing serves to limit the rate at which the food may pass through the UES and downward into the esophagus. The bulking devices may be surgically or endoscopically implanted within the UES of the patient.

The bulking devices may be expandable following implantation. In some embodiments, the bulking device includes a solid, hydrogel material that is expandable. In particular, the hydrogel material may be at least partially dehydrated prior to implantation, and then expand substantially due to rehydration following implantation.

In one embodiment, the invention provides method for treatment of obesity, the method comprising implanting one or more bulking devices in a region of an upper esophageal sphincter (UES) of a patient.

In another embodiment, the invention provides a system for treatment of obesity, the system comprising an endoscopic delivery device sized for introduction into an esophagus of a patient, a bulking device for implantation in a mucosal wall of an upper esophageal sphincter (UES) of the esophagus, wherein the implanted bulking devices are sized to expand the UES to create a partial occlusion of an inner lumen of the esophagus proximate the UES or partially impair function of a muscle associated with the UES, and a placement tool, deliverable via the endoscopic delivery device, to implant the bulking device in a region of the UES.

In a further embodiment, the invention provides a system for treatment of obesity, the system comprising an endoscopic delivery device sized for introduction into an esophagus of a patient, bulking means, implantable in a mucosal wall of an upper esophageal sphincter (UES) of the esophagus, for bulking the UES to create a partial occlusion of an inner lumen of the esophagus proximate the UES or partially impair function of a muscle associated with the UES, and means for implanting the bulking means device in a region of the UES via the endoscopic delivery device.

Various embodiments of the invention may provide one or more advantages. By partially obstructing the UES, or partially impairing the function of muscles associated with the UES, the patient is incapable of consuming food at an excessive rate, and experiences discomfort during excessive food consumption. The partial obstruction physically limits excessive food consumption, while the discomfort provides a form of biofeedback that discourages the patient from excessive eating. The result is prevention of increased obesity and possibly weight loss. In this manner, the invention is capable of discouraging excessive consumption of food without the use of appetite suppressant medications or chronic implantation of prostheses within the interior of the stomach. Also, in some embodiments, implantation of the bulking devices can be achieved endoscopically without the need for invasive surgical intervention or modification of the stomach structure. In this manner, the invention provides for a simple, safe, minimally invasive technique for achieving weigh loss in obese patients. Consequently, the invention can treat obesity with reduced side effects, reduced recovery time, and possible elimination of lengthy hospital stays.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
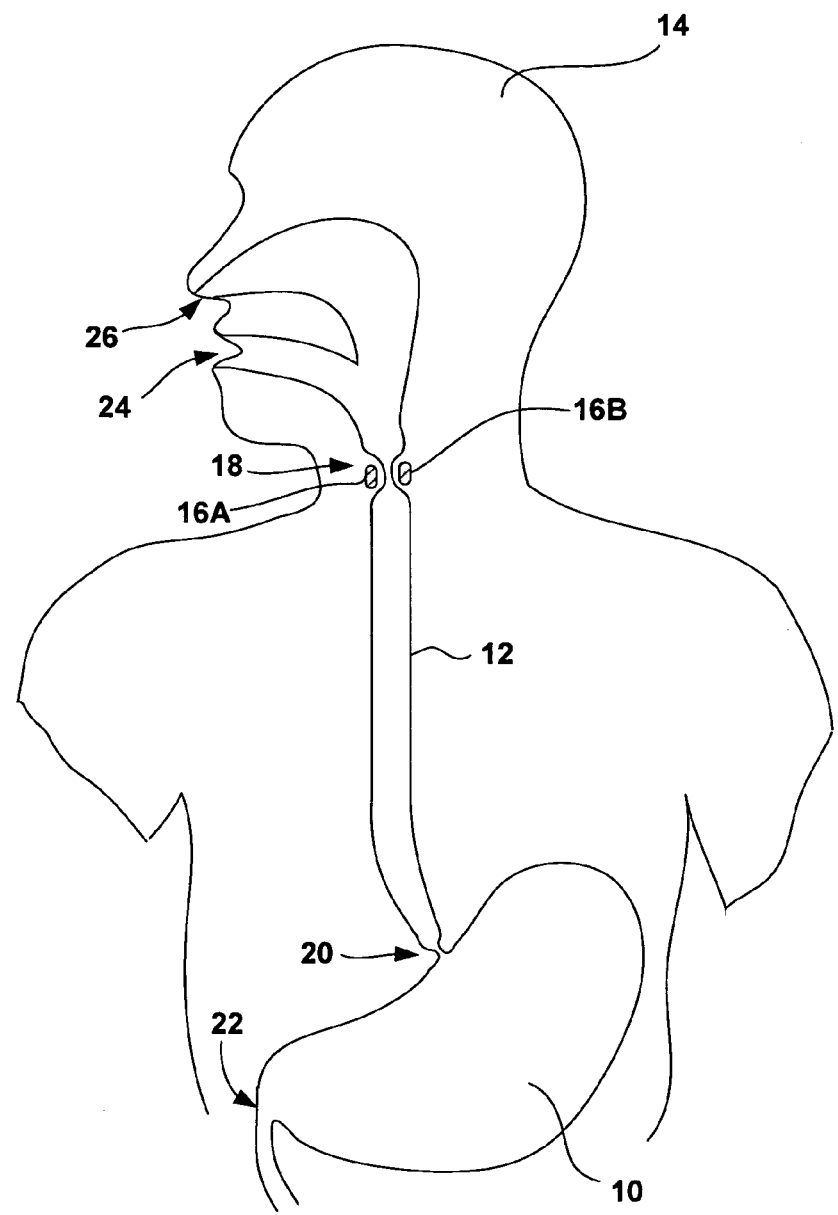
FIG. 1 is a cross-sectional diagram of the interior of the esophagus and stomach with bulking devices implanted in the UES to inhibit swallowing.

FIG. 1 is a cross-sectional diagram of the interior of a stomach 10 and esophagus 12 of a patient 14 with bulking devices 16A, 16B (hereinafter bulking devices 16) implanted within UES 18 to inhibit swallowing, in accordance with the invention. As shown in FIG. 1, esophagus 12 extends downward to join stomach 10 at lower esophageal sphincter (LES) 20, which regulates input to the stomach. Pyloric sphincter 22 joins stomach and the small intestine, and regulates output of stomach 10. UES 18 is positioned between the oral passage 24 of patient 14 and esophagus 12, and regulates passage of food from the oral passage into the esophagus. Bulking devices 16 are implanted within UES to make swallowing difficult, and thereby discourage patient 14 from ingesting food at an excessive rate. Although FIG. 1 illustrates two bulking devices 16 in cross-section, additional bulking devices may be implanted at different angular positions about the circumference of UES 18.

UES 18 is in a region at the top of esophagus 12. The region of UES 18 is approximately two to four centimeters in length, and separates the pharynx (not shown) from esophagus 12. UES 18 generally includes the region from the distal part of the cricoid cartilage, to the crycopharyngeus muscle, and to a portion of the inferior constrictor muscle. The cricoid cartilage and the crycopharyngeus muscle lie approximately adjacent to cervical spine segment C5. Bulking devices 16 may be implanted within the oblique or horizontal fibers of the crycopharyngeus or inferior constrictor muscles, or within the sub-mucosal region of the UES. Each of these regions extends generally between cervical spine segments C6 and C4. Bulking devices 16 bulk the UES region so that the patient 14 experiences difficulty in opening the UES to swallow food.

The swallowing difficulty experienced by patient 14 serves to limit food intake by a patient, and cause weight loss over a period of time, thereby treating obesity. In particular, patient 14 is incapable of consuming food at an excessive rate, and experiences discomfort during excessive food consumption. The partial obstruction physically limits excessive food consumption through esophagus 12. At the same time, the discomfort may provide a form of biofeedback that discourages patient 14 from consuming food at an excessive rate. The result is prevention of increased obesity and weight loss over an extended period of time. In some cases, bulking devices 16 may be explanted from patient 14 after a desired amount of weight loss has been achieved.

Weight loss often occurs in patients who have difficulty swallowing, a condition known as dysphagia. Patients afflicted with dysphagia have difficulty swallowing and passing food from the mouth, through the esophagus, and into the stomach. This condition may be caused by abnormalities affecting the neuromuscular mechanisms of the smooth muscle in the mouth pharynx and upper esophageal sphincter (UES), and is referred to as oropharyngeal dysphagia. Oropharyngeal dysphagia may occur due to failure of the upper esophageal muscles to relax sufficiently during the swallowing reflex. This can be caused by certain forms of muscular dystrophy or cancers of the central nervous system or esophagus.

Implantation of bulking devices 16 within UES 18 may simulate symptoms of oropharyngeal dysphagia, resulting in weight loss similar to that experience by patient suffering from actual oropharyngeal dysphagia. In particular, bulking devices 16 can create a controlled form of oropharyngeal dysphagia by placement of an inert bulking device into the region of the UES 18 as a means of inducing weight loss in obese patients. Although food intake is limited, patient 18 is still able to ingest a sufficient amount of food to support nutritional requirements.

Bulking devices 16 may be implanted surgically or endoscopically, although endoscopic implantation ordinarily will be desirable. In particular, endoscopic implantation of bulking devices 16 via oral passage 24, or possibly nasal passage 26, can prevent substantial trauma and recovery time otherwise associated with surgical implantation techniques. Endoscopic implantation may reduce the duration and complexity of the implantation procedure, and possibly eliminate the need for an overnight hospital stay in some instances. In addition, endoscopic implantation may be less likely to disrupt the physiological function of UES 18, stomach 10, esophagus 12, and LES 20.

Bulking devices 16 may be formed from an expandable material that is initially implanted with a reduced, unexpanded size. Upon implantation, bulking devices 16 expand to a larger size to stretch the region around UES 18 and inhibit swallowing. As an example, a bulking device 16 may be a prosthesis formed from a hydrogel material that is implanted in an at least partially dehydrated state having a reduced size. Upon rehydration following implantation, bulking devices 16 assume an expanded state and increased size. Hence, the initial, unexpanded size of bulking devices 16 facilitates implantation, but subsequent expansion makes swallowing more difficult.

In the example of FIG. 1, bulking devices 16 have a substantially cylindrical shape. In other embodiments, bulking devices 16 may have a variety of shapes, e.g., substantially spherically shaped, rod-shaped, tube-shaped, disc-shaped, curved, flat, or irregularly shaped. In some embodiments, bulking devices 16 may carry a radio-opaque filler agent such as $BaSO_4$ or Ta. In an at least partially dehydrated state for implantation, a cylinder-shaped bulking device 16 may have a diameter of approximately 2 mm, and a length of approximately 20 mm. Following implantation in UES 18, the capsule-shaped bulking device 16 may have a diameter of approximately 5.5 to 6.0 mm and a length of approximately 10 to 15 mm. This corresponds to an exemplary pre-implantation volume of less than approximately 65 $mm^3$ and a post-implantation volume of greater than or equal to approximately 400 $mm^3$.

Hence, in general, in an at least partially dehydrated state for implantation, each bulking device 16 may have a volume of less than approximately 100 $mm^3$. Upon expansion following implantation and subsequent rehydration, bulking device 16 may have a volume of greater than approximately 200 $mm^3$. In some embodiments, each bulking device 16 may have a pre-implantation volume of less than or equal to approximately 75 mm$^3$ and a post-implantation volume of greater than or equal to approximately 300 mm$^3$. Hence, the hydrogel material may have an expansion ratio of greater than or equal to approximately 100 percent, or greater than or equal to approximately two times the pre-implantation size.

In some embodiments, however, each bulking device 16 may have a larger volumetric expansion ratio, from an at least partially dehydrated state (pre-implantation) to a hydrated, expanded state (post-implantation), of at least approximately 4.5:1, and more particularly approximately 27:1. Other sizes and expansion ratios may be selected in accordance with the structural requirements for formation of a partial obstruction and the thickness of the esophageal wall in a given patient.

Bulking devices 16 may be placed at a series of regularly or irregularly spaced angular positions about the circumference of UES 18. In some embodiments, two, three, four or more bulking devices 16 may be placed in UES 18. Spacing between adjacent bulking devices 16 may be controlled by taking into account the expanded size of the bulking devices. Adjacent bulking devices 16 may be separated about the circumference of UES 18 by a section of intact mucosal tissue or muscle within the wall of esophagus 12. By leaving a substantial portion of the mucosal tissue or muscle intact, bulking devices 16 can inhibit swallowing without substantially compromising the physiological function or structural integrity of esophagus 12 in the digestion process.

Figure 2:
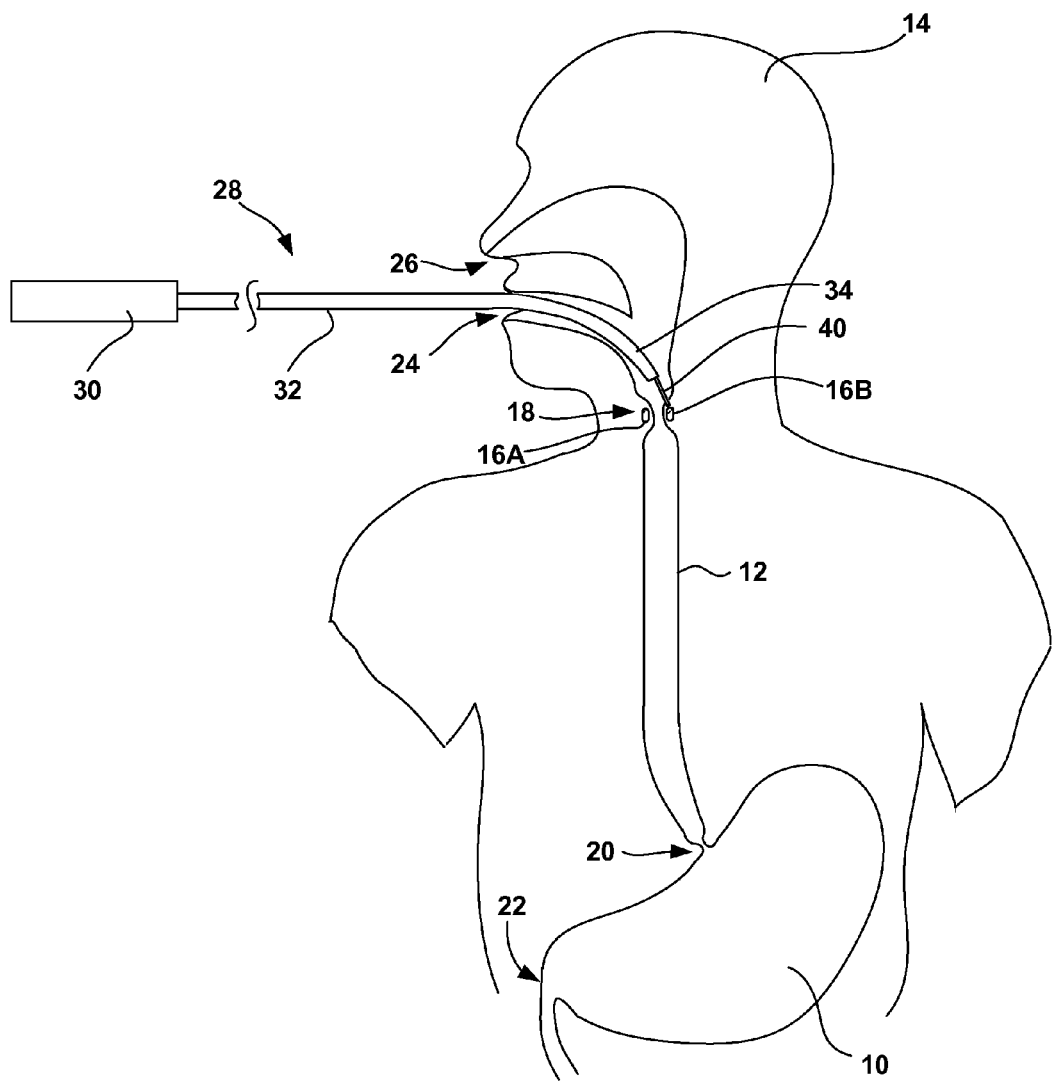
FIG. 2 is a diagram illustrating deployment of an endoscopic delivery device shown in conjunction with an esophagus and stomach of a patient.

FIG. 2 is a diagram illustrating deployment of an endoscopic delivery system 28 shown in conjunction with a stomach 10 of a patient 14. As shown in FIG. 2, endoscopic delivery system 28 serves to position and place bulking devices 16 within UES 18 of patient 14. Endoscopic delivery system 28 includes a proximal portion, referred to herein as a handle 30, and a flexible probe 32 that extends from handle 30 into the gastrointestinal tract of patient 14 via oral passage 24.

A bulking device 16 is delivered to a target location in the UES 18 via a distal end 34 of flexible probe 32. In particular, one or more placement tools 40 may extend distally or laterally from distal end 34 of flexible probe for preparation of an implantation pocket and implantation of a bulking device 16. Distal end 34 of flexible probe 32 accesses UES 18, via either oral passage 24 or nasal passage 26, and extends to a desired location above UES 18. Upon implantation of a bulking device 16, endoscopic flexible probe 32 may be repositioned to implant other bulking devices within UES 18.

Figure 3:
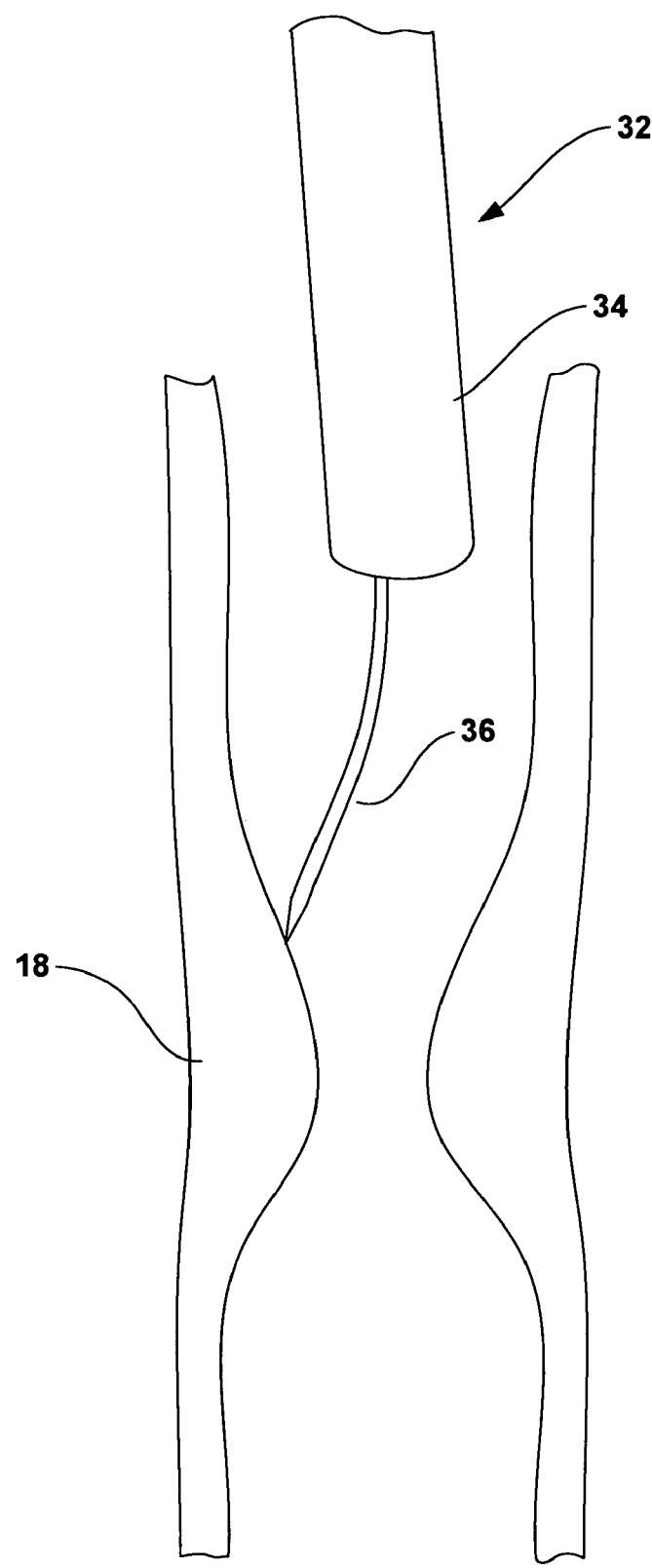
FIG. 3 is an enlarged view of a portion of the esophagus in the vicinity of the UES, illustrating preparation of an implantation pocket for a bulking device.

FIG. 3 is an enlarged view of a portion of the esophagus 12 in the vicinity of the UES 18, illustrating optional preparation of an implantation pocket for a bulking device 16. Formation of an implantation pocket prior to implantation of bulking device 16 may not be be necessary. As will be described, however, the formation of an implantation pocket may be advantageous in that it serves to stretch and define a sub-mucosal area beneath the mucosal wall, or between muscle layers, of UES 18 to provide space to receive the bulking device 16, and perhaps accommodate some of the expansion of the bulking device.

Figure 4:
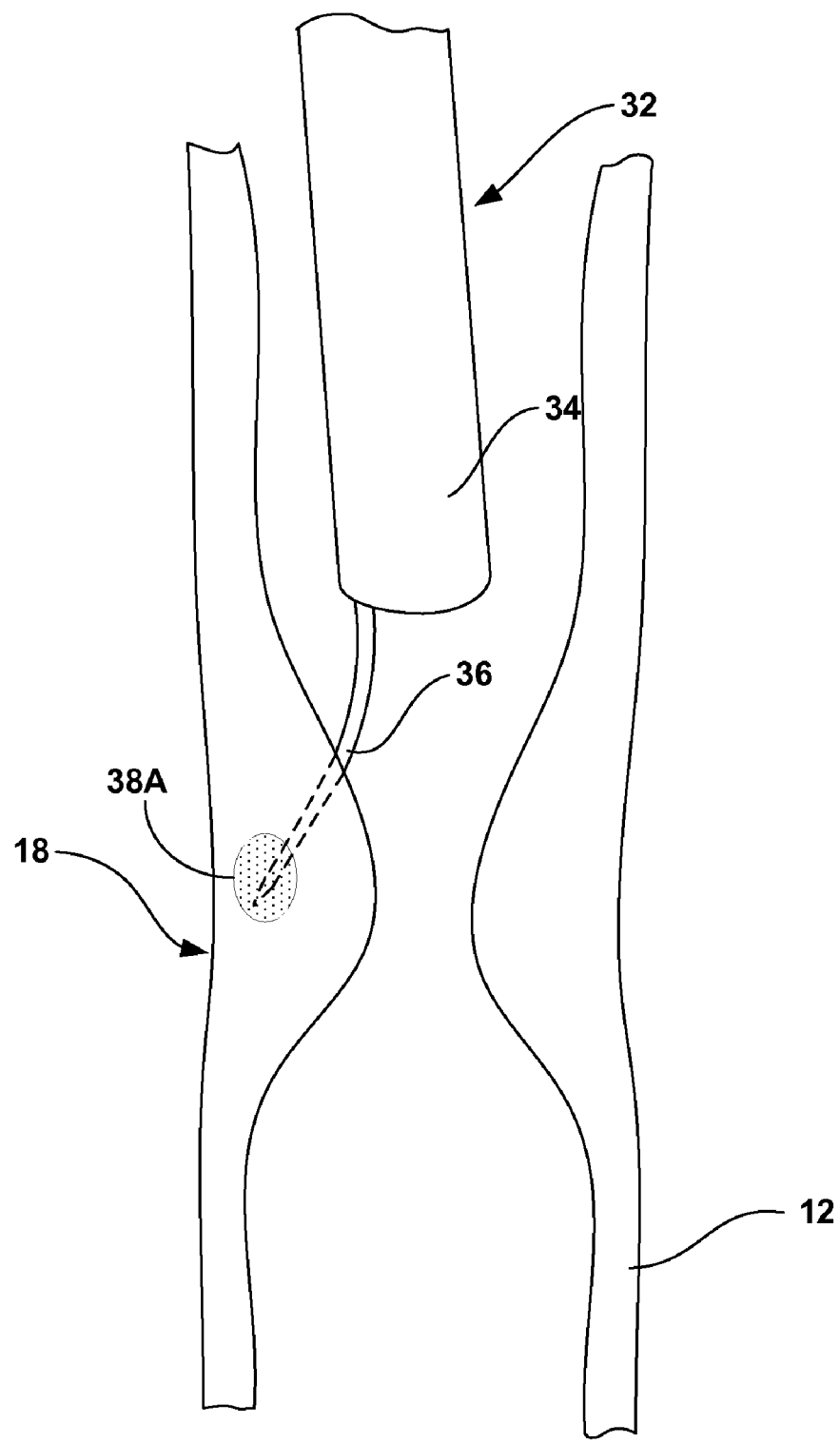
FIG. 4 is another enlarged view of a portion of the esophagus in the vicinity of the UES, illustrating injection of a fluid to prepare an implantation pocket.

FIG. 4 is another enlarged view of a portion of the esophagus 12 in the vicinity of the UES 18, illustrating injection of a fluid 38A to prepare an implantation pocket. Formation of the implantation pocket may be optional, and may not be necessary in some embodiments. As shown in FIGS. 3 and 4, a physician extends a needle 36 along the length of flexible probe 32 and out from distal end 34 to penetrate the mucosal wall of esophagus 12 adjacent UES 18.

For example, the physician may steer distal end 34 of flexible probe 32 to a desired location on the mucosal wall using conventional endoscope. Upon penetration of the mucosal wall, the physician injects a bolus of saline or other biocompatible fluid to expand a localized region of the mucosal wall and create a sub-mucosal implantation pocket. In this case, the bulking device 16 is implanted within the mucosal wall at UES 18. Alternatively, the physician may guide needle 36 into a muscle layer within UES 18 and create the implantation pocket in the muscle layer. In this case, the bulking device 16 is implanted within or between muscle layers.

When bulking device 16 is implanted beneath the mucosal wall, swallowing is inhibited due to the increased bulking of UES 18. Specifically, bulking device 16 causes UES 18 to extend inward, creating a smaller opening when UES 18 relaxes during swallowing. In this case, UES 18 is operable but presents a smaller passage for food. When bulking device 16 is implanted within or between muscle layers at UES 18, the bulking device may likewise cause UES 18 to extend inward. However, the bulking device 16 may additionally impair the function of the muscles in the UES 18, at least partially, so that the patient experiences difficulty in swallowing. In this case, UES 18 may present a smaller passage for food, but also may be partially impaired, making swallowing more difficult.

Figure 5:
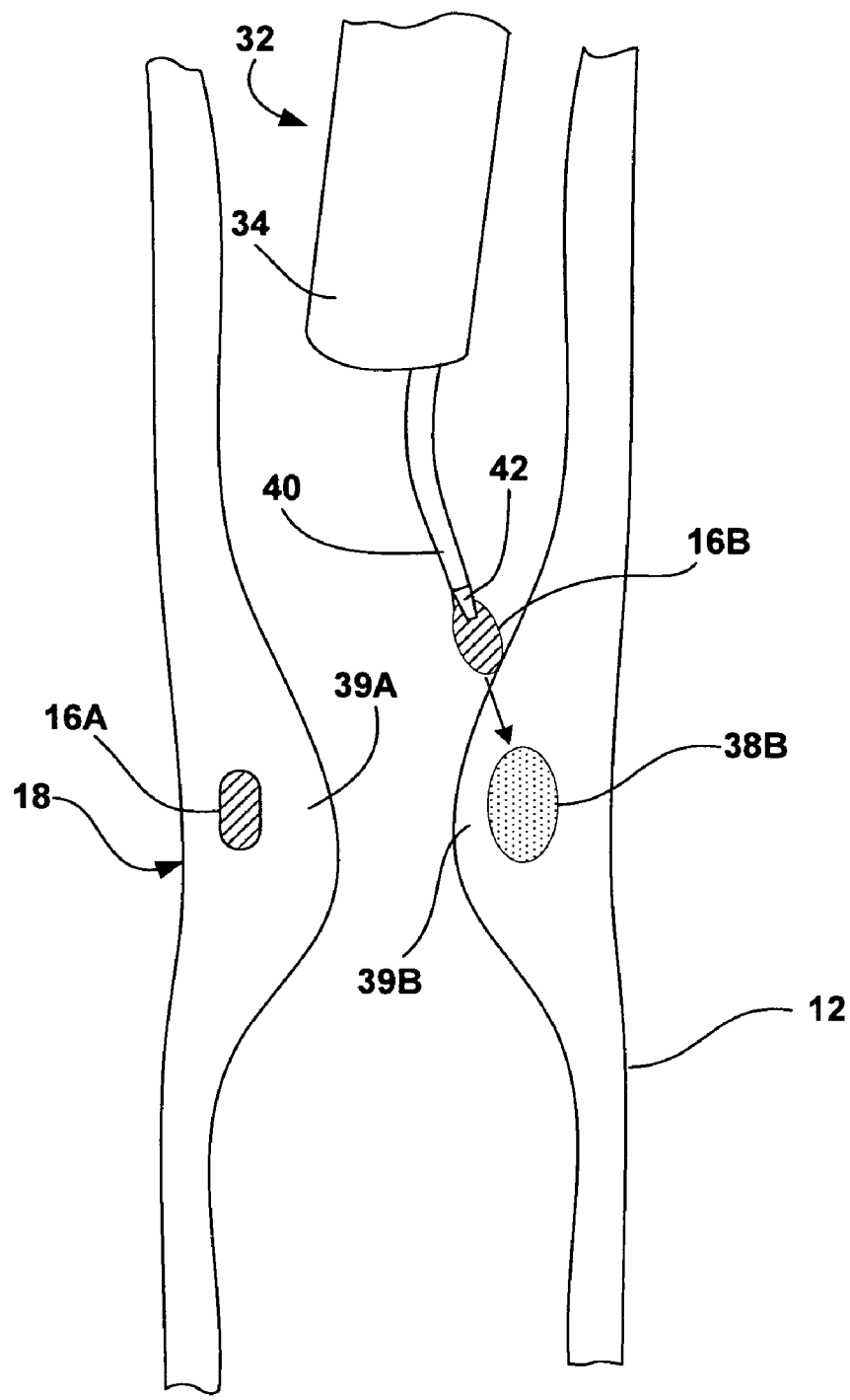
FIG. 5 is another enlarged view of a portion of the esophagus in the vicinity of the UES, illustrating placement of a bulking device in an implantation pocket.

FIG. 5 is another enlarged view of a portion of the esophagus 12 in the vicinity of UES 18, illustrating placement of a bulking device 16B in implantation pocket 39B. In FIG. 5, bulking device 16A is shown following implantation in implantation pocket 39A. Bulking device 16B is shown in the process of implantation. In particular, bulking device 16B is implanted into implantation pocket 39B via an aperture formed in a mucosal wall of UES 18. The aperture may be formed by a cutting tool or blunt dissection. A placement tool 40 extends along the length of flexible probe 32 and protrudes from a distal end 34 of the flexible probe. Placement tool 40 may be independently steerable to locate the desired implantation pocket 39B created by fluid 38B.

In the example of FIG. 5, placement tool 40 includes a gripping member 42, such as a pair of jaws or forceps, that carry bulking device 16B for placement within implantation pocket 39B. Upon placement of bulking device 16B within implantation pocket 39B, a suture or stapling tool may be introduced via flexible probe 32 to close the aperture in the mucosal lining. Precise positioning may be aided by endoscopic viewing provided by an imaging endoscope integrated within or delivered simultaneously with flexible probe 32. In addition, external imaging techniques such as fluoroscopy or ultrasonic imaging may be used to aid precise positioning. Another placement approach is described in U.S. Pat. No. 6,401,718 to Johnson et al., assigned to Medtronic Endonetics, Inc., and entitled "Submucosal esophageal bulking device," the entire content of which is incorporated herein by reference.

As discussed above, bulking device 16B may be implanted sub-mucosally under the mucosal lining of the UES 18, or within or between muscle layers. The depth of implantation may be controlled according to the length of placement tool 40. Also, radiographic imaging may be used to view the placement of bulking device 16B relative to cervical spine sections C4, C5 and C6.

As an alternative (not shown) to implantation with a gripping member, in some embodiments, a bulking device 16B may be initially mounted in a tip of a needle, which may be introduced via flexible probe 32. Upon placement of the tip of needle within the wall of UES 18 at a desired implantation site, a physician expels bulking device 16B from the needle. The physician may actuate a fluid pressure source or elongated push rod to drive bulking device 16B out of the needle and into the wall of UES 18. Following implantation via the needle, bulking device expands, e.g., by rehydration, to assume an enlarged size.

Then, the needle and flexible probe 32 may be withdrawn or repositioned to implant another bulking device 16 at a different tissue site within the esophageal wall. As an example, the needle may have a diameter in the range of less than approximately 2 mm to 4 mm in inside diameter, which can accommodate a spherical or rod-like bulking device 16 having a diameter or transverse cross-section, respectively, of approximately 1.5 mm to 3.5 mm in diameter. Upon implantation of bulking device 16 with a needle, the implantation hole may be sufficiently small that there is not a need for suturing or stapling.

Figure 6:
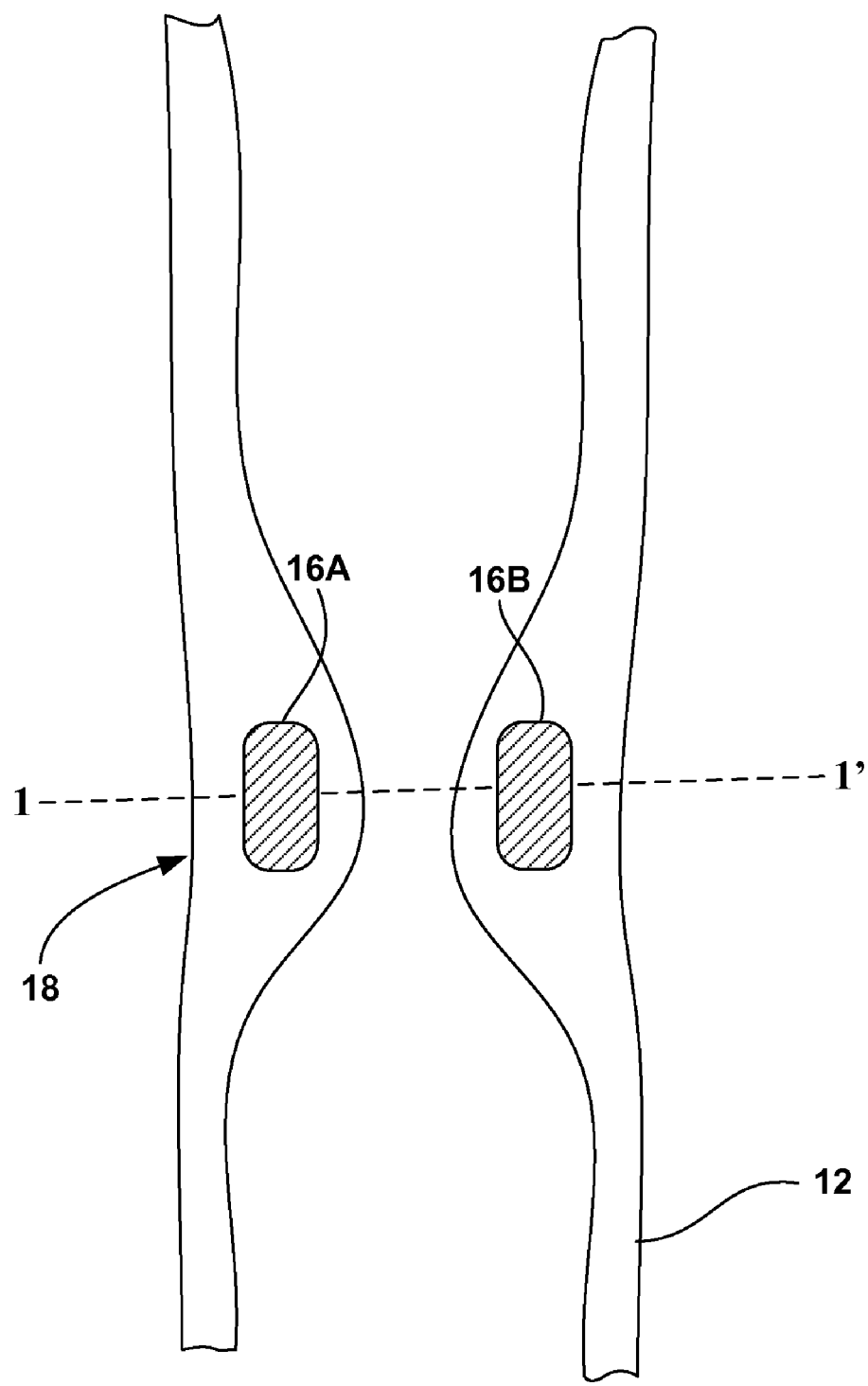
FIG. 6 is an enlarged view of a portion of the esophagus in the vicinity of the UES, illustrating expansion of bulking devices following implantation to produce a partial obstruction in the esophagus.

FIG. 6 is an enlarged view of a portion of the esophagus 12 in the vicinity of the UES 18, illustrating expansion of bulking devices 16 following implantation within UES 18. Bulking device 18 create a partial obstruction by extending UES 18 inward in the lumen defined by esophagus 12, creating a partial obstruction, or partially impairs the operation of muscles associated with UES 18. In either cases, swallowing is made more difficult. In FIG. 5, bulking devices 16 are shown at the time of implantation in an initial, unexpanded state. In FIG. 6, however, bulking devices 16 are shown following implantation in an expanded state. As discussed above, bulking devices 16 may be formed from a variety of expandable materials that permit implantation of the bulking devices in an initial, reduced size, followed by post-implant expansion to inhibit swallowing by patient 14.

As an example, bulking devices 16 may be formed from a hydrogel material that is implanted in an at least partially dehydrated state. In a dehydrated state, the hydrogel materials is reduced in size. Following implantation, bulking device 16 takes on moisture and rehydrates. In this manner, bulking device 16 expands to an enlarged size that further increases the degree of inward extension of UES 18, or further impairs UES muscle function. A hydrogel material may be implanted as a solid prosthesis, as shown in FIGS. 3-6, or injected as a fluid material that becomes solid or semi-solid following injection.

Bulking devices 16 may be implanted at any desired position with the region defined by UES 18. The length of the esophagus varies from patient to patient, but is on the order of approximately 25 cm. UES 18 is approximately two to four centimeters in length, and separates the pharynx (not shown) from esophagus 12. UES 18 generally includes the region from the distal part of the cricoid cartilage, the crycopharyngeus muscle, and a portion of the inferior constrictor muscle. In typical patients, UES 18 resides between 8 and 12 cm below the back of oral passage 24, i.e., the back of the mouth.

Again, the cricoid cartilage and the crycopharyngeus muscle lie adjacent to cervical spine segments C4-C6. Accordingly, bulking device 16 may be implanted in the vicinity of cervical spine segments C4-C6, either within the oblique or horizontal fibers of the crycopharyngeus or inferior constrictor muscles, or within the sub-mucosal region of UES 18. In other embodiments, rather than being placed within UES 18, bulking devices 16 may be formed within approximately 1 to 2 cm above or below the UES.

Figure 7:
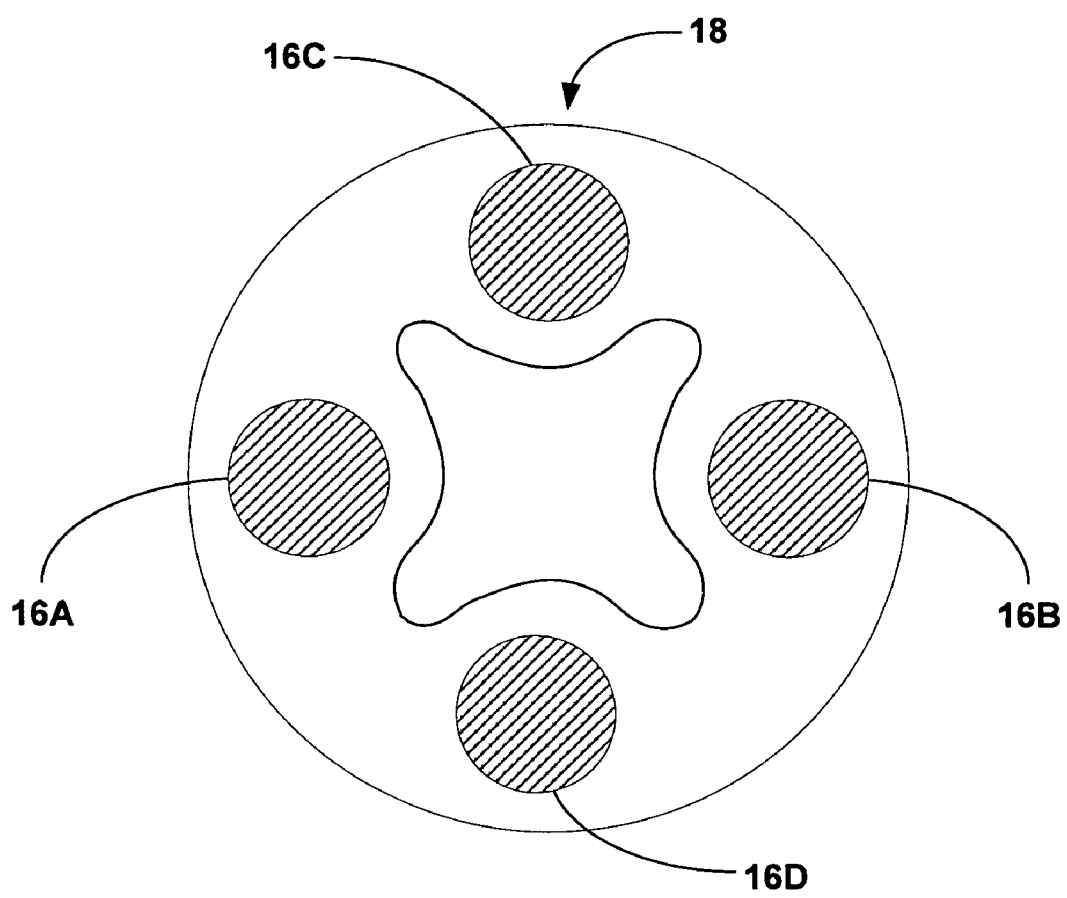
FIG. 7 is a cross-sectional end view of the esophagus taken across line 1-1' of FIG. 6, illustrating implantation of multiple bulking devices within the UES.

FIG. 7 is a cross-sectional end view of the UES 18 taken across line 1-1' of FIG. 6, illustrating implantation of a plurality of implanted bulking devices 16A, 16B visible in FIG. 6 and additional bulking devices 16C, 16D. In the example of FIG. 7, individual bulking devices 16A-16D are implanted at angular positions spaced approximately 90 degrees apart from one another around UES 18. In this manner, bulking devices 16A-16D contribute to a combined effect of impairing UES muscle operation or creating a partial obstruction of the inner lumen of esophagus 12 in the vicinity of UES 18. The number of bulking devices 16 implanted in UES 18 may vary, and may be more or less than the number of bulking devices shown in the example of FIG. 7.

Figure 8:
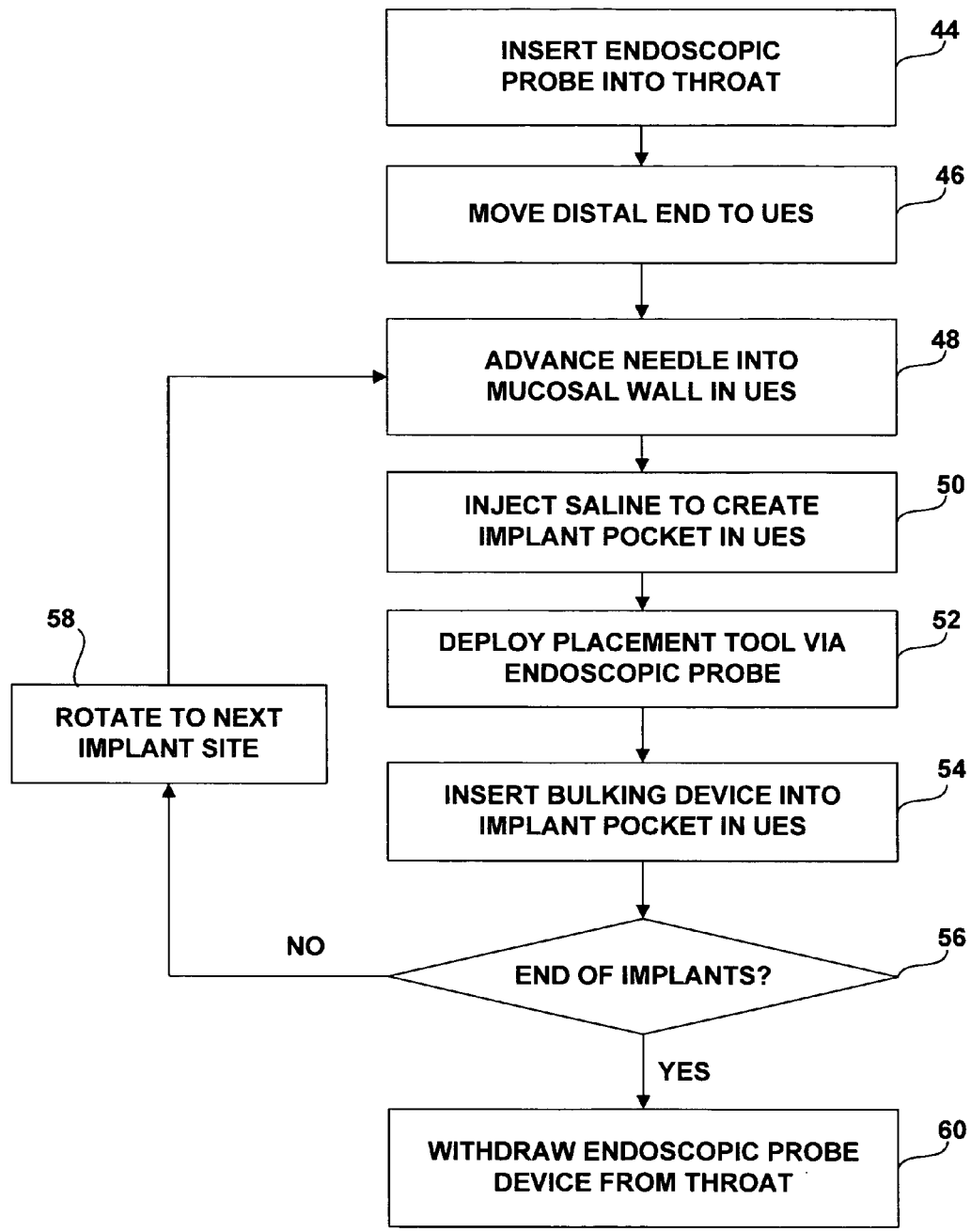
FIG. 8 is a flow diagram illustrating a method for implanting a bulking device in the UES to inhibit swallowing.

FIG. 8 is a diagram illustrating a method for implanting a bulking device 16 in UES 18 of patient 14. As shown in FIG. 8, a physician inserts an endoscopic delivery device into the throat of a patient 14 (44), via the oral or nasal passage, and moves a distal end of a flexible probe to UES 18 (46). The physician then advances a needle from the distal end of the flexible probe and into a mucosal wall in the vicinity of UES 18 (48). Once the distal tip of the needle is in place, the physician injects saline or another fluid into the mucosal wall to create an implantation pocket (50).

The physician then withdraws the needle, and deploys a placement tool via the flexible probe (52), and implants the bulking device into the implant pocket (54). The placement tool may take the form of a needle or gripping device. If additional bulking devices are to be implanted (56), the physician repositions the flexible probe to another implant site (58) in the UES 18 and repeats the implantation process. When all bulking devices have been implanted, the physician withdraws the endoscopic delivery device from the esophagus (60).

A bulking device 16, as described herein, preferably is soft and compliant to minimize trauma within UES 18 upon implantation. The bulking device may be constructed from a variety of inert and biocompatible materials, including polymeric materials. Again, the materials forming bulking device may be expandable. In particular, as described herein, the bulking devices may be formed from an expandable hydrogel material. As further alternatives, bulking devices 16 may be formed from silicone rubber or polyurethane, with or without radio-opaque filler agents, such as $BaSO_4$ or Ta. Suitable materials, including hydrogel materials, are described in U.S. Pat. No. 6,401,718 to Johnson et al., assigned to Medtronic Endonetics, Inc., and entitled "Submucosal esophageal bulking device," the entire content of which is incorporated herein by reference.

Hydrogel materials, as described in the Johnson et al. patent, may be desirable as they can be readily fabricated in a variety of shapes, including cylindrical or capsule shapes that can be easily implanted. In addition, hydrogel materials advantageously can be implanted in a dehydrated state, making the bulking device smaller upon implant, and further minimizing the surgical trauma associated with the implant procedure. After implant, the hydrogel material absorbs moisture from the body of the patient and expands to its final size.

As alternatives, described in the Johnson et al. patent, bulking device 16 may take the form of a fluid-filled, flexible capsule, pillow or balloon made from elastomeric materials such as silicone, latex, urethane, and the like. Example fillers include biocompatible liquid or gel such as saline, silicone oil, dimethyl sulfoxide (DMSO), polyvinyl, pyrollidone and hydrogels. As a further alternative, the bulking device may be a unitary structure formed by molding, casting, stamping or the like. The unitary structure may formed from hydrogel material, biocompatible foam material such as silicone foam or polyurethane foam, or a variety of biocompatible materials such as silicone, polyurethane, polysulfone, polyester, and the like. As described in Johnson et al., foam material may include outer skin of porous foam that facilitates tissue ingrowth.

As alternatives to implanted solid materials, bulking devices 16 may be formed by injected fluids that form solids following injection. Examples of injectable bulking devices are those marketed by Boston Scientific as part of the Enteryx procedure, or those marketed by Carbon Medical Technologies, Inc, as the Durasphere GR Injectable Bulking Agent, which includes pyrolytic carbon-coated beads suspended in a water-based carrier gel. A variety of implanted solid materials and injected fluids suitable for formation of bulking devices to form a partial obstruction of the esophagus, as described herein, are disclosed in U.S. Published Patent Application No. 20040019388, to Starkebaum, assigned to Medtronic, Inc. and entitled "Methods and implants for retarding stomach emptying to treat eating disorders," the entire content of which is incorporated herein by reference. Accordingly, bulking devices may refer to solid, semi-solid, or filled implants, or injected fluids that formed solid or semi-solid bulking devices within UES 18 to treat obesity.

Many embodiments of the invention have been described. Various modifications may be made without departing from the scope of the claims. These and other embodiments are within the scope of the following claims.

The invention claimed is:

1. A method for treatment of obesity, the method comprising implanting in an obese patient selected for treatment of obesity one or more bulking devices having one or more characteristics selected to limit food intake into an esophagus of a patient in a region of an upper esophageal sphincter (UES) of the patient; and explanting the bulking devices from the patient when the patient has achieved a desired amount of weight loss.

2. The method of claim 1, further comprising implanting the bulking devices in a sub-mucosal region of the UES.

3. The method of claim 1, further comprising implanting the bulking devices within a muscle layer of the UES.

4. The method of claim 1, further comprising implanting the bulking devices between muscle layers of the UES.

5. The method of claim 1, further comprising implanting the bulking devices within oblique fibers of a crycopharyngeus muscle of the UES.

6. The method of claim 1, further comprising implanting the bulking devices within oblique fibers of an inferior constrictor muscle of the UES.

7. The method of claim 1, further comprising implanting the bulking devices within horizontal fibers of a crycopharyngeus muscle of the UES.

8. The method of claim 1, further comprising implanting the bulking devices within horizontal fibers of an inferior constrictor muscle of the UES.

9. The method of claim 1, wherein the bulking devices are implanted and sized to at least partially obstruct the UES.

10. The method of claim 1, wherein the bulking devices are implanted and sized to at least partially impair function of a muscle associated with the UES.

11. The method of claim 1, further comprising endoscopically implanting the bulking devices within the UES of the patient.

12. The method of claim 1, further comprising repositioning an endoscopic device among a plurality of implantation sites to endoscopically implant a plurality of the bulking devices.

13. The method of claim 1, wherein each of the bulking devices includes a solid, hydrogel material.

14. The method of claim 13, further comprising implanting the bulking devices with the hydrogel material in an at least partially dehydrated state, the bulking devices rehydrating upon implantation and thereby expanding in size to expand the UES.

15. The method of claim 1, wherein the bulking devices are expandable following implantation.

16. The method of claim 15, wherein the bulking devices are expandable from a pre-implantation volume of less than approximately 100 mm$^3$ to a post-implantation size of greater than or equal to approximately 200 mm$^3$.

17. The method of claim 16, wherein the bulking devices are expandable from a pre-implantation size to a post-implantation size of greater than or equal to approximately two times the pre-implantation size.

18. The method of claim 1, wherein each of the bulking devices is substantially capsule-like in shape, substantially spherical in shape, substantially disc-like in shape, or substantially rod-like in shape.

19. The method of claim 1, further comprising implanting a plurality of the bulking devices at different angular positions about the inner lumen of the esophagus.

20. The method of claim 19, wherein the bulking devices include four bulking devices spaced at approximately 90 degree intervals from one another.

21. The method of claim 1, further comprising injecting a fluid into a mucosal wall to create an implantation pocket, and implanting one of the bulking devices in the implantation pocket.

22. A method for treatment of obesity, the method comprising:
identifying an obese patient for obesity treatment; and
implanting one or more bulking devices in a region of an upper esophageal sphincter (UES) of the identified patient such that the implanted bulking devices limit food intake by the patient and thereby treat obesity.

23. The method of claim 22, further comprising implanting the bulking devices in a sub-mucosal region of the UES.

24. The method of claim 22, further comprising implanting the bulking devices at least one of within a muscle layer of the UES or between muscle layers of the UES.

25. The method of claim 22, further comprising implanting the bulking devices within at least one of oblique or horizontal fibers of a crycopharyngeus muscle of the UES.

26. The method of claim 22, further comprising implanting the bulking devices within at least one of oblique or horizontal fibers of an inferior constrictor muscle of the UES.

27. The method of claim 22, wherein the bulking devices are implanted and sized to at least one of partially obstruct the UES or partially impair function of a muscle associated with the UES.

28. The method of claim 22, wherein each of the bulking devices includes a solid, hydrogel material, the method further comprising implanting the bulking devices with the hydrogel material in an at least partially dehydrated state, the bulking devices rehydrating upon implantation and thereby expanding in size to expand the UES.

29. The method of claim 22, wherein the bulking devices are expandable from a pre-implantation size to a post-implantation size of greater than or equal to approximately two times the pre-implantation size.

30. The method of claim 22, wherein each of the bulking devices is substantially capsule-like in shape, substantially spherical in shape, substantially disc-like in shape, or substantially rod-like in shape.

31. The method of claim 22, further comprising implanting a plurality of the bulking devices at different angular positions about the inner lumen of the esophagus, wherein the bulking devices include four bulking devices spaced at approximately 90 degree intervals from one another.

32. The method of claim 22, further comprising injecting a fluid into a mucosal wall to create an implantation pocket, and implanting one of the bulking devices in the implantation pocket.

33. The method of claim 22, further comprising explanting the bulking devices from the patient when the patient has achieved a desired amount of weight loss.

34. The method of claim 22, further comprising endoscopically implanting the bulking devices within the UES of the patient.

35. The method of claim 22, further comprising repositioning an endoscopic device among a plurality of implantation sites to endoscopically implant a plurality of the bulking devices.

* * * * *